United States Patent [19]

Henrick

[11] 4,248,875

[45] Feb. 3, 1981

[54] PYRIDYL ESTERS AND THIOLESTERS OF α-SUBSTITUTED UNSATURATED ACIDS

[75] Inventor: Clive A. Henrick, Palo Alto, Calif.

[73] Assignee: Zoecon Corporation, Palo Alto, Calif.

[21] Appl. No.: 71,435

[22] Filed: Aug. 31, 1979

[51] Int. Cl.³ .................. C07D 213/30; C07D 213/32
[52] U.S. Cl. .................................... 424/263; 542/427;
546/298; 546/302; 546/301; 546/328; 546/314;
546/341; 546/340; 546/330; 546/334; 546/335
[58] Field of Search ........................ 542/427; 424/263;
546/298, 301, 302, 328, 314, 341, 340, 330, 335, 334

[56] References Cited

U.S. PATENT DOCUMENTS

| 3,567,743 | 3/1971 | Anderson | 542/427 |
| 4,163,787 | 12/1977 | Malhotra et al. | 424/263 |
| 4,172,135 | 7/1978 | Kristiansen et al. | 424/263 |
| 4,204,071 | 5/1980 | Anderson et al. | 560/100 |

*Primary Examiner*—Arthur P. Demers
*Attorney, Agent, or Firm*—Donald W. Erickson

[57] ABSTRACT

Pyridyl esters and thiolesters of α-substituted unsaturated acids, intermediates therefor, synthesis thereof and the use of said esters and thiolesters and compositions for the control of pests.

20 Claims, No Drawings

PYRIDYL ESTERS AND THIOLESTERS OF α-SUBSTITUTED UNSATURATED ACIDS

This invention relates to novel esters and thiolesters of α-substituted unsaturated acids, novel intermediates therefor, synthesis thereof, and the control of pests.

The esters of thiolesters of the present invention are represented by the following formula (A):

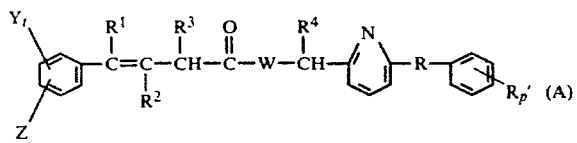

wherein, p is zero, one or two;
t is zero, one, two, three or four;
W is oxygen or sulfur;
Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro, and lower haloalkylthio;
Z is independently selected from the values of Y, cycloalkyl, and lower haloalkoxy; or Y and Z form a methylenedioxy group;
R is oxygen, sulfur, methylene or carbonyl;
R' is fluoro, bromo, chloro, trifluoromethyl, methyl, methoxy or methylthio;
each of $R^1$ and $R^2$ is independently selected from hydrogen, chloro, fluoro, bromo, lower alkyl, lower alkenyl, lower alkoxy, cycloalkalkyl, and lower haloalkyl;
$R^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms, or lower cycloalkyl of 3 or 4 carbon atoms;
$R^4$ is hydrogen, cyano, ethynyl, methyl, trifluoromethyl or thioamide; and the salt thereof of a strong inorganic acid or organic acid.

The compounds of the present invention represented by formula (A) are useful agents for the control of pests such as insects and acarids.

In the description hereinafter and the appended claims, each of R through $R^4$, W, Y, Z, p and t is as defined hereinabove, unless otherwise specified.

The compounds of formula (A) can be synthesized as outlined below.

reacted with an alcohol of formula II in an organic solvent such as diethyl ether in the presence of triethylamine. In another embodiment, an acid of formula I and an alcohol of formula II are reacted in an organic solvent such as methylene chloride in the presence of 4-dimethylaminopyridine and dicyclohexylcarbodiimide to form an ester of formula A'. In another synthesis, the acid of formula I or salt thereof is reacted with the bromide, chloride or mesylate of the alcohol for formula II to form an ester of formula A'. The starting materials of formula I are described in the copending application of Anderson and Henrick, U.S. Pat. No. 4,204,071. The alcohols of formula II can be made as described by Malhotra and Ricks, U.S. Pat. No. 4,163,787, and Maeda and Hirose, CA 81 135964k and 80 59873s and references cited therein.

The thiolesters of formula (A) can be prepared by the reaction of the acid of formula I with the S-thiol corresponding to the alcohol of formula II in the presence of oxalyl chloride and dimethylaminopyridine and an organic solvent such as tetrahydrofuran or dimethylformamide.

The following terms, wherever used in the description herein and the appended claims, have the meaning defined below, unless otherwise specified hereinafter.

The term "lower alkyl" refers to an alkyl group, straight or branched, having a chain length of one to eight carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to eight carbon atoms. The term "lower alkylthio" refers to an alkylthio group, straight or branched, having a chain length of one to eight carbon atoms.

The term "lower alkenyl" refers to an ethylenically unsaturated hydrocarbon group, straight or branched, having a chain length of two to eight carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms.

The term "cycloalkyl" refers to a cycloalkyl group of three to eight cyclic carbon atoms. The term "cycloalkalkyl" refers to a cycloalkyl group wherein one hydrogen atom is replaced by a lower alkyl group, the total number of carbon atoms being from four to twelve, such as cyclopropanemethyl, cyclobutaneethyl, cyclohexanemethyl, and the like.

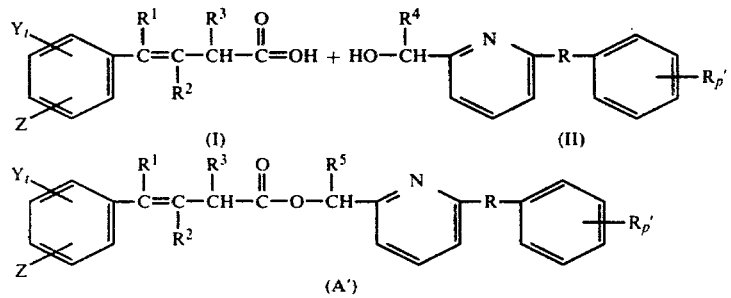

In the general practice of the above synthesis, an acid, salt thereof or the acid chloride is reacted with an alcohol of formula II to form the carboxylic ester A'. For example, an acid chloride of the acid of formula I is The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

The compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g. propoxur, carbaryl, naled, dichlorvos, phosmet, chlorpyrifos, acephate, diazinon, methoprene, kinoprene, hydroprene, cyhexatin, resmethrin, permethrin and fenvalerate.

The following examples are provided to illustrate the practice of the present invention. Temperature is given in degrees Centigrade. RT means room temperature.

EXAMPLE 1

To a solution of 0.93 g (4.18 mmol) of 4-(4-fluorophenyl)-2-isopropyl-3-butenoic acid in 25 ml benzene, cooled in an ice bath under nitrogen, is added 0.5 ml (5.7 mmol) of oxalyl chloride over 10 minutes, followed by 3 drops dimethylformamide. The reaction mixture is warmed to RT and stirred for 90 minutes, after which the solution is evaporated under reduced pressure, then dissolved in 20 ml dry ether. To one-half of the resulting solution is added a solution of 0.418 g (2.08 mmol) (6-phenoxy-2-pyridyl) methane and 1.3 ml (9.5 mmol) triethylamine in 5 ml ether. The reaction mixture is stirred for 90 minutes, then quenched with aqueous sodium bicarbonate and diluted with water. The organic phase is washed with water (2×), saturated aqueous sodium bicarbonate (2×), saturated aqueous sodium chloride (2×), and dried over calcium sulfate and solvent is evaporated. The crude product is chromatographed on a circular chromatograph eluting with 15 percent ether/hexane to yield (6-phenoxy-2-pyridyl) methyl 4-(4-fluorophenyl)-2-isopropyl-3-butenoate, MS m/e 405 (M+).

EXAMPLE 2

A. To a solution of 6-phenoxypyridyl-2-carboxaldehyde (0.37 g, 1.8 mmol) in 25 ml of ether is added 25 ml of water followed by sodium cyanide (0.149 g, 3.04 mmol). The mixture is stirred vigorously while a solution of sodium bisulfite (0.257 g, 2.47 mmol) in 15 ml of water is added over about 5 minutes. The reaction mixture is stirred for two hours. The organic phase is separated, washed with water, dried over calcium sulfate and solvent evaporated to give cyano (6-phenoxy-2-pyridyl) methanol.

B. To the acid chloride of 4-(4-fluorophenyl)-2-isopropyl-3-butenoic acid in ether, under nitrogen, is added 1.3 ml of triethylamine followed by the cyano (6-phenoxy-2-pyridyl) methanol (1.5 mmol) in 5 ml of ether, from part A above, over about 2 minutes. The reaction mixture is stirred for about 18 hours and then quenched with saturated aqueous sodium bicarbonate. The organic phase is washed with aqueous sodium bicarbonate, water and brine, dried over calcium sulfate and solvent evaporated. The crude product is chromatographed on a circular chromatograph eluting with 15 percent ether/hexane to give cyano (6-phenoxy-2-pyridyl) methyl 4-(4-fluorophenyl)-2-isopropyl-3-butenoate, MS m/e 430 (M+).

EXAMPLE 3

To a stirred solution of cyano (6-phenoxy-2-pyridyl) methanol (1.8 mmol), 4-(2-chloro-4-trifluoromethylphenyl)-2-isopropyl-3-butenoate (2.0 mmol) and dimethylaminopyridine (0.65 mmol) in 20 ml of methylene chloride and 2 ml of dimethylformamide is added N,N'-dicyclohexylcarbodiimide (2.0 mmol). The reaction mixture is stirred, under nitrogen, for two hours and then filtered and extracted with water. The aqueous phase is extracted with ether. The combined organic phases are washed with saturated aqueous sodium bicarbonate, water and saturated aqueous sodium chloride, dried over calcium sulfate and solvent evaporated. The crude product is chromatographed on a rotary chromatograph eluting with 25 percent ether/hexane to yield the cyano(6-phenoxy-2-pyridyl) methyl 4-(2-chloro-4-trifluoromethylphenyl)-2-isopropyl-3-butenoate.

EXAMPLE 4

Following the procedure of Example 3, each of the acids under column I is converted to the ester under column II by reaction with cyano(6-phenoxy-2-pyridyl) methanol.

I 2-isopropyl-4-(4-methoxyphenyl)-3-butenoic acid
2-isopropyl-4-(4-methylphenyl)-3-butenoic acid
4-(3-chlorophenyl)-2-isopropyl-3-butenoic acid
2-isopropyl-4-(2-trifluoromethylphenyl)-3-butenoic acid 2-isopropyl-4-pentafluorophenyl-3-butenoic acid
4-(4-cyclopropylphenyl)-2-isopropyl-3-butenoic acid
2-isopropyl-4-(t-butylphenyl)-3-butenoic acid
2-isopropyl-4-(4-methylthiophenyl)-3-butenoic acid
4-(2-fluoro-4-trifluoromethylphenyl)-2-isopropyl-3-butenoic acid
4-(3,4-dichlorophenyl)-2-isopropyl-3-butenoic acid
4-(3-fluoro-4-methylphenyl)-2-isopropyl-3-butenoic acid
4-(4-chloro-2,6-difluorophenyl)-2-isopropyl-3-butenoic acid

II cyano(6-phenoxy-2-pyridyl)methyl 2-isopropyl-4-(4-methoxyphenyl)-3-butenoate
cyano (6-phenoxy-2-pyridyl)methyl 2-isopropyl-4-(4-methylphenyl)-3-butenoate
cyano(6-phenoxy-2-pyridyl)methyl 4-(3-chlorophenyl)-2-isopropyl-3-butenoate
cyano(6-phenoxy-2-pyridyl)methyl 2-isopropyl-4-(2-trifluoromethylphenyl)-3-butenoate
cyano(6-phenoxy-2-pyridyl)methyl 2-isopropyl-4-pentafluorophenyl-3-butenoate
cyano(6-phenoxy-2-pyridyl)methyl 4-(4-cyclopropylphenyl)-2-isopropyl-3-butenoate
cyano(6-phenoxy-2-pyridyl)methyl 2-isopropyl-4-(t-butylphenyl)-3-butenoate
cyano(6-phenoxy-2-pyridyl)methyl 2-isopropyl-4-(4-methylthiophenyl)-3-butenoate
cyano(6-phenoxy-2-pyridyl)methyl 4-(2-fluoro-4-trifluoromethylphenyl)-2-isopropyl-3-butenoate
cyano(6-phenoxy-2-pyridyl)methyl 4-(3,4-dichlorophenyl)-2-isopropyl-3-butenoate
cyano(6-phenoxy-2-pyridyl)methyl 4-(3-fluoro-4-methylphenyl)-2-isopropyl-3-butenoate
cyano(6-phenoxy-2-pyridyl)methyl 4-(4-chloro-2,6-difluorophenyl)-2-isopropyl-3-butenoate

EXAMPLE 5

The acid chloride of 2-isopropyl-4-chloro-4-phenyl-3-butenoic acid is reacted with (6-phenoxy-2-pyridyl)methanol using the procedure of Example 1 to give (6-phenoxy-2-pyridyl)methyl 2-isopropyl-4-chloro-4-phenyl-3-butenoate.

In the same manner, (6-phenoxy-2-pyridyl)methyl 2-isopropyl-3-methyl-4-phenyl-3-butenoate is prepared by the reaction of 2-isopropyl-3-methyl-4-phenyl-3-butenoic acid with (6-phenoxy-2-pyridyl)methanol.

EXAMPLE 6

The acid chloride of 4-(2-chloro-4-trifluoromethylphenyl)-2-isopropyl-3-butenoic acid is reacted with cyano[6-(4-fluorophenoxy)-2-pyridyl] methanol in ether as in Example 2 to give cyano[6-(4-fluorophenoxy)-2-pyridyl] methyl 4-(2-chloro-4-trifluoromethylphenyl)-2-isopropyl-3-butenoate.

By the procedure of Example 1, the acid chloride of each of 4-(4-fluorophenyl)-2-isopropyl-3-butenoic acid and 4-(4-chlorophenyl)-2-isopropyl-3-butenoic acid is reacted with [6-(4-fluorophenoxy)-2-pyridyl] methanol, yielding [6-(4-fluorophenoxy)-2-pyridyl]methyl 4-(4-fluorophenyl)-2-isopropyl-3-butenoate and [6-(4-fluorophenoxy)-2-pyridyl]methyl 4-(4-chlorophenyl)-2-isopropyl-3-butenoate, respectively.

EXAMPLE 7

Oxalyl chloride (1.65 mmol) and dimethylformamide are added, at RT, to 4-(4-fluorophenyl)-2-isopropyl-3-butenoic acid (0.92 mmol) in 10 ml benzene. After all gas evolution has stopped, about 5 minutes, the solution is warmed to 40°, then stripped of solvent and excess oxalyl chloride. The residue is brought up in tetrahydrofuran, and (6-phenoxy-2-pyridyl)methane thiol (0.92 mmol) and dimethylaminopyridine are added with stirring. Stirring is continued for 18 hours, after which the solution is brought up in ether, washed with water (3×) and brine, and dried oversodium sulfate to give S-(6-phenoxy-2-pyridyl)methyl thioester of 4-(4-fluorophenyl)-2-isopropyl-3-butenoic acid.

In the same manner, methyl (6-phenoxy-2-pyridyl) methane thiol and 4-(4-fluorophenyl)-2-isopropyl-3-butenoic acid are reacted, yielding S-methyl (6-phenoxy-2-pyridyl) methyl thioester of 4-(4-fluorophenyl)-2-isopropyl-3-butenoic acid.

Preparation of the compound (6-phenoxy-2-pyridyl) methane thiol is described in my application Ser. No. 069,446, filed on or about Aug. 24, 1979.

EXAMPLE 8

Following the method of Example 3, (6-phenylthio-2-pyridyl) methanol is reacted with each of 4-(4-fluorophenyl)-2-isopropyl-3-butenoic acid, 4-(2-chloro-4-trifluoromethylphenyl)-2-isopropyl-3-butenoic acid, 4-(4-chlorophenyl)-2-isopropyl-3-butenoic acid and 4-pentafluorophenyl-2-isopropyl-3-butenoic acid to yield
(6-phenylthio-2-pyridyl)methyl 4-(4-fluorophenyl)-2-isopropyl-3-butenoate,
(6-phenylthio-2-pyridyl)methyl 4-(2-chloro-4-trifluoromethylphenyl)-2-isopropyl-3-butenoate,
(6-phenylthio-2-pyridyl)methyl 4-(4-chlorophenyl)-2-isopropyl-3-butenoate, and
(6-phenylthio-2-pyridyl)methyl 4-pentafluorophenyl-2-isopropyl-3-butenoate.

EXAMPLE 9

Following the procedure of Example 3, each of methyl(6-phenoxy-2-pyridyl)methanol and methyl[6-(4-fluorophenoxy)-2-pyridyl]methanol is reacted with 4-(4-fluorophenyl)-2-isopropyl-3-butenoic acid to yield methyl(6-phenoxy-2-pyridyl)methyl 4-(4-fluorophenyl)-2-isopropyl-3-butenoate and methyl[6-(4-fluorophenoxy)-2-pyridyl]methyl 4-(4-fluorophenyl)-2-isopropyl-3-butenoate, respectively.

Further, ethynyl(6-phenoxy-2-pyridyl) methyl 4-(4-fluorophenyl)-2-isopropyl-3-butenoate is made from 4-(4-fluorophenyl)-2-isopropyl-3-butenoic acid and ethynyl(6-phenoxy-2-pyridyl) methanol.

EXAMPLE 10

The compounds (6-benzoyl-2-pyridyl)methanol is reacted with 4-(4-chlorophenyl)-2-isopropyl-3-butenoic acid or 4-(4-fluorophenyl)-2-isopropyl-3-butenoic acid, following the procedure of Example 3, to give (6-benzoyl-2-pyridyl)methyl 4-(4-chlorophenyl)-2-isopropyl-3-butenoate or (6-benzoyl-2-pyridyl)methyl 4-(4-fluorophenyl)-2-isopropyl-3-butenoate. (6-Benzoyl-2-pyridyl)methanol is prepared as described in my application Ser. No. 069,446, filed on or about Aug. 24, 1979.

EXAMPLE 11

Following the procedure of Example 1, the acid chloride of each of 4-(4-fluorophenyl)-2-isopropyl-3-butenoic acid, 4-(2-chloro-4-trfluoromethylphenyl)-2-isopropyl-3-butenoic acid and 4-(2-fluoro-4-trifluoromethylphenyl)-2-isopropyl-3-butenoic acid is reacted with (6-benzyl-2-pyridyl)methanol to give (6-benzyl-2-pyridyl)methyl 4-(4-fluorophenyl)-2-isopropyl-3-butenoate,
(6-benzyl-2-pyridyl)methyl 4-(2-chloro-4-trifluoromethylphenyl)-2-isopropyl-3-butenoate, and
(6-benzyl-2-pyridyl)methyl 4-(2-fluoro-4-trifluoromethylphenyl)-2-isopropyl-3-butenoate.

The procedure for making (6-benzyl-2-pyridyl)methanol is described in my application Ser. No. 069,446, filed on or about Aug. 24, 1979.

EXAMPLE 12

To 15 ml of dimethylformamide and 10 ml of tetrahydrofuran is added 1.60 mmol of the thio acid of 4-(4-fluorophenyl)-2-isopropyl-3-butenoic acid, KHCO$_3$ (4.01 mmol) and the mesylate of α-cyano-(6-phenoxy-2-pyridyl)-methanol (1.60 mmol). The reaction mixture is stirred at RT for about 18 hours. The mixture is taken up in ether, washed with water and brine, dried over sodium sulfate and solvent stripped to give S-α-cyano-(6-phenoxy-2-pyridyl) methyl thioester of 4-(4-fluorophenyl)-2-isopropyl-3-butenoic acid.

Two groups of 10 each of 0–24 hour III instar *Heliothis virescens* larvae were treated with 1 μl of the compound, cyano (6-phenoxy-2-pyridyl)methyl 4-(4-fluorophenyl)-2-isopropyl-3-butenoate, in acetone at five different concentrations by application to the dorsum of the thorax. Two groups of 10 each are treated identically with 1 μl acetone only as controls. Larvae are held individually in 30 ml plastic cups provided with artificial medium for 72 hours at 25° and 16 hr photoperiod. After 72 hours the number of dead is calculated as a percentage of the total number originally treated and then corrected for any mortality in the control groups using Abbott's formula. The LD$_{50}$ of the compound was less than 0.1%.

What is claimed is:

1. A compound of the formula (A):

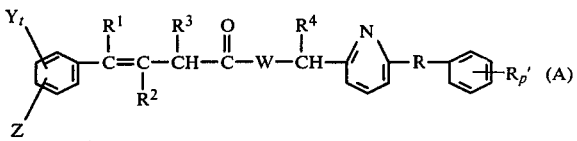

wherein,
p is zero, one or two;
t is zero, one, two, three or four;
W is oxygen or sulfur;
Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro, and lower haloalkylthio;
Z is independently selected from the values of Y, cycloalkyl, and lower haloalkoxy; or Y and Z form a methylenedioxy group;
R is oxygen, sulfur, methylene or carbonyl;
R' is fluoro, bromo, chloro, trifluoromethyl, methyl, methoxy or methylthio;
each of R$^1$ and R$^2$ is independently selected from hydrogen, chloro, fluoro, bromo, lower alkyl, lower alkenyl, lower alkoxy, cycloalkalkyl, and lower haloalkyl;
R$^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms, or lower cycloalkyl of 3 or 4 carbon atoms;
R$^4$ is hydrogen, cyano, ethynyl, methyl, trifluoromethyl or thioamide; and the salt thereof of a strong inorganic acid or organic acid.

2. A compound according to claim 1 of the formula:

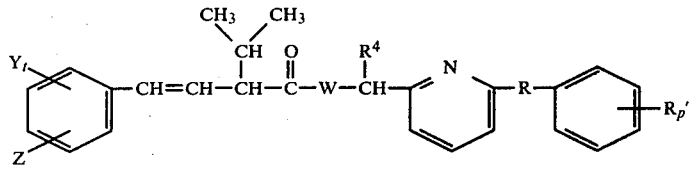

3. A compound according to claim 2 wherein R$^4$ is hydrogen, cyano or methyl.
4. A compound according to claim 3 wherein p is zero or one.
5. A compound according to claim 4 wherein Y is hydrogen, methyl, chloro or fluoro and Z is hydrogen, methyl, chloro, fluoro or trifluoromethyl.
6. A compound according to claim 5 wherein p is zero or one.
7. A compound according to claim 6 wherein t is zero and Z is in the para position.
8. A compound according to claim 7 wherein W is oxygen and R is oxygen.
9. A compound according to claim 8 wherein R' is fluoro.
10. A compound according to claim 7 wherein W is oxygen and R is carbonyl.
11. A compound according to claim 10 wherein R' is fluoro.
12. A compound according to claim 7 wherein W is sulfur, R is oxygen and R' is fluoro.
13. A compound according to claim 12 wherein R$^4$ is hydrogen.
14. A compound according to claim 7 wherein W is sulfur, R is carbonyl and R' is fluoro.
15. A compound according to claim 14 wherein R$^4$ is hydrogen.
16. A compound according to claim 6 wherein t is four, and each of Y and Z is fluoro.
17. A compound according to claim 16 wherein W is oxygen, R is oxygen or carbonyl, and R' is fluoro.
18. A compound according to claim 16 wherein W is sulfur, R is oxygen or carbonyl, and R' is fluoro.
19. A compound according to claim 18 wherein R$^4$ is hydrogen.
20. A process for the control of insects and acarids which comprises applying to the locus in a pesticidally effective amount a compound of the following formula (A):

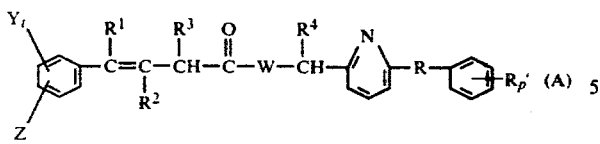

wherein, p is zero, one or two;

t is zero, one, two, three or four;

W is oxygen or sulfur;

Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro, and lower haloalkylthio;

Z is independently selected from the values of Y, cycloalkyl, and lower haloalkoxy; or Y and Z form a methylenedioxy group;

R is oxygen, sulfur, methylene or carbonyl;

R' is fluoro, bromo, chloro, trifluoromethyl, methyl, methoxy or methylthio;

each of $R^1$ and $R^2$ is independently selected from hydrogen, chloro, fluoro, bromo, lower alkyl, lower alkenyl, lower alkoxy, cycloalkalkyl, and lower haloalkyl;

$R^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms, or lower cycloalkyl of 3 or 4 carbon atoms;

$R^4$ is hydrogen, cyano, ethynyl, methyl, trifluoromethyl or thioamide; and the salt thereof of a strong inorganic acid or organic acid.

* * * * *